United States Patent
Houser, Jr.

(10) Patent No.: US 9,925,127 B2
(45) Date of Patent: Mar. 27, 2018

(54) FLAVORED GENITAL HYGIENE TOWELETTE, ASSEMBLY AND METHOD OF USE

(71) Applicant: Funky Junk, Inc., Broomall, PA (US)

(72) Inventor: Timothy Paul Houser, Jr., Broomall, PA (US)

(*) Notice: Subject to any disclaimer, the term of this patent is extended or adjusted under 35 U.S.C. 154(b) by 0 days.

(21) Appl. No.: 14/876,989

(22) Filed: Oct. 7, 2015

(65) Prior Publication Data

US 2016/0151250 A1 Jun. 2, 2016

Related U.S. Application Data

(60) Provisional application No. 62/062,222, filed on Oct. 10, 2014.

(51) Int. Cl.
| | |
|---|---|
| *A61K 8/02* | (2006.01) |
| *A61Q 19/10* | (2006.01) |
| *B65D 75/12* | (2006.01) |
| *B65D 75/58* | (2006.01) |
| *A61Q 19/00* | (2006.01) |
| *B65D 83/08* | (2006.01) |

(52) U.S. Cl.
CPC .......... *A61K 8/0208* (2013.01); *A61Q 19/005* (2013.01); *A61Q 19/10* (2013.01); *B65D 75/12* (2013.01); *B65D 75/5838* (2013.01); *B65D 83/0805* (2013.01); *B65D 2575/586* (2013.01)

(58) Field of Classification Search
None
See application file for complete search history.

(56) References Cited

U.S. PATENT DOCUMENTS

| | | |
|---|---|---|
| 6,624,198 B1 | 9/2003 | Porat |
| 8,156,598 B2 | 4/2012 | McDowell |
| 2002/0192268 A1 | 12/2002 | Alwattari |
| 2004/0242097 A1* | 12/2004 | Hasenoehrl ........ A44B 18/0011 442/59 |
| 2006/0275241 A1* | 12/2006 | Padlo ................ A61K 8/0208 424/70.16 |
| 2008/0274164 A1 | 11/2008 | Vollmer |
| 2010/0158986 A1* | 6/2010 | Decker ............... A61K 8/0208 424/443 |
| 2010/0197544 A1 | 8/2010 | De La Cruz |
| 2013/0037049 A1 | 2/2013 | Kulichkov |
| 2013/0108722 A1 | 5/2013 | Stangler |
| 2015/0044309 A1 | 2/2015 | Davies |

* cited by examiner

*Primary Examiner* — Necholus Ogden, Jr.
(74) *Attorney, Agent, or Firm* — Panitch Schwarze Belisario & Nadel LLP

(57) ABSTRACT

A personal hygiene towelette includes a consumable cleaning solution that includes a cleaning agent and a flavoring agent, as well as a textile fabric body, for example a nonwoven textile fabric body, impregnated with the cleaning solution. A personal hygiene assembly including the towelette may further include a sealed housing that houses the personal hygiene towelette.

13 Claims, 4 Drawing Sheets

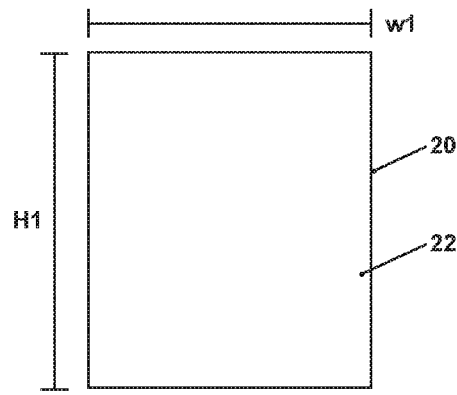
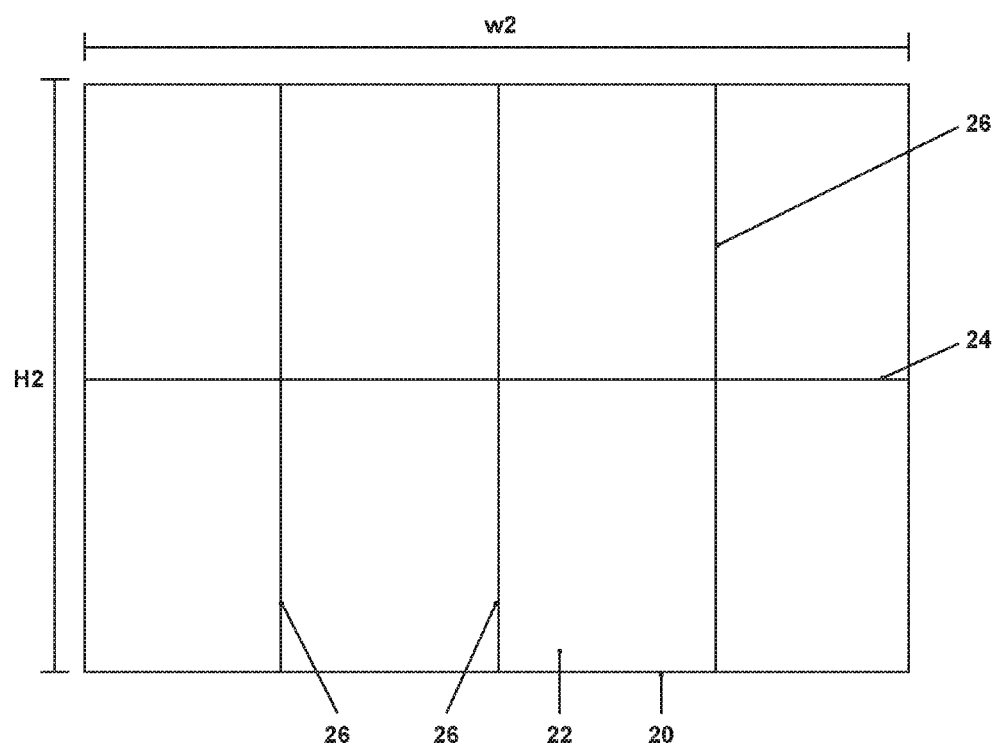

Fig. 7
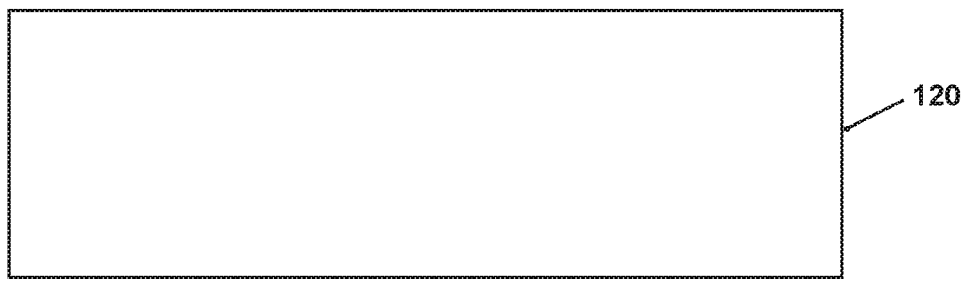
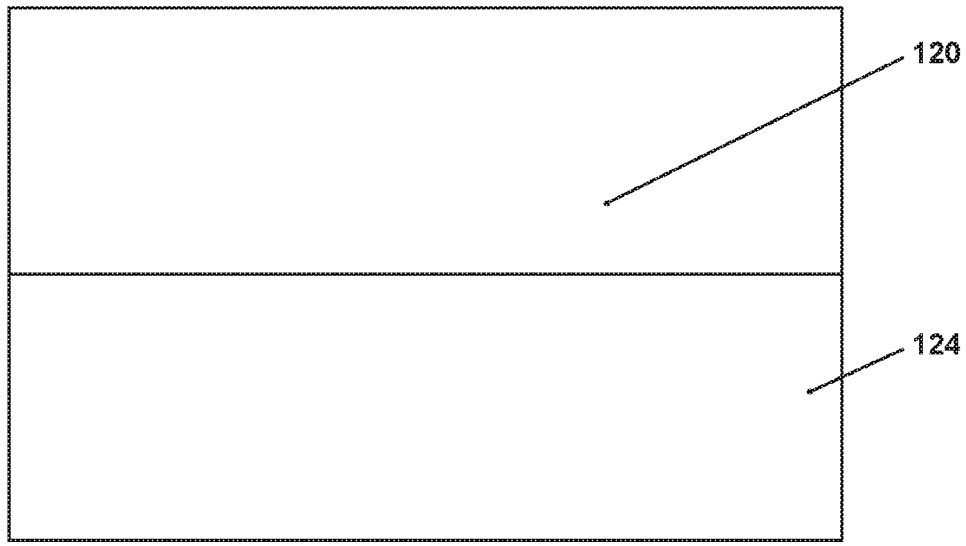
Fig. 8

FLAVORED GENITAL HYGIENE TOWELETTE, ASSEMBLY AND METHOD OF USE

CROSS REFERENCE TO RELATED APPLICATION

This application claims the benefit of U.S. Provisional Patent Application No. 62/062,222, filed Oct. 10, 2014, which is incorporated by reference as if fully set forth.

FIELD OF INVENTION

The invention pertains generally to personal hygiene towelettes, and more particularly to flavored personal hygiene towelettes for use on or about the genital area.

BACKGROUND

Both men and women may be concerned about hygiene as related to their groin and genital regions prior to a sexual encounters. Many individuals may not have the opportunity to bathe before such encounters, particularly in instances following a long evening of partying and/or dancing, which may often precede such sexual encounters. Products such as flavored lubricants are known in the art, and their widespread use indicates that it may be desirable to create a pleasant flavor on and around the genital area for purposes of sexual encounters. Often however, there may be little or no access to proper hygiene materials and sexual aid products prior to a romantic encounter.

A need exists for a personal hygiene product that can be discreetly carried on one's person, such as in an individual's purse or pocket, and which can conveniently be used and disposed of, for example, within a restroom, with little preparation. A further need exists for a product that can conveniently dispense a pleasant flavor about an individual's genital region in preparation for a sexual encounter.

SUMMARY

The invention relates to a personal hygiene towelette, including a consumable cleaning solution having a cleaning agent and a flavoring agent, as well as a textile fabric body impregnated with the cleaning solution.

The invention further relates to a personal hygiene assembly including a personal hygiene towelette. The towelette includes a consumable cleaning solution including a cleaning agent and a flavoring agent, as well as a textile fabric body impregnated with the cleaning solution. A sealed housing houses the personal hygiene towelette.

The invention further relates to a method of genital cleansing. The method includes providing a personal hygiene assembly. The personal hygiene assembly includes a personal hygiene towelette, which includes a consumable cleaning solution having a cleaning agent and a flavoring agent, and a textile fabric body impregnated with the cleaning solution. A housing including a seal houses the personal hygiene towelette. The method further includes breaking the seal and removing the personal hygiene towelette from the housing, and wiping a user's genital area with the personal hygiene towelette, such that the consumable cleaning solution is deposited on the genital area during wiping.

BRIEF DESCRIPTION OF THE DRAWINGS

FIG. 3 is a top plan view of the towelette of the assembly of FIG. 1, in a folded configuration.

FIG. 4 is a top plan view of the towelette of the assembly of FIG. 1, in an unfolded configuration.

FIG. 7 is a top plan view of one of the towelettes of the assembly of FIG. 6, in a folded configuration.

FIG. 8 is a top plan view of the one of the towelettes of the assembly of FIG. 6, in an unfolded configuration.

DETAILED DESCRIPTION OF THE PREFERRED EMBODIMENTS

Figure 1:
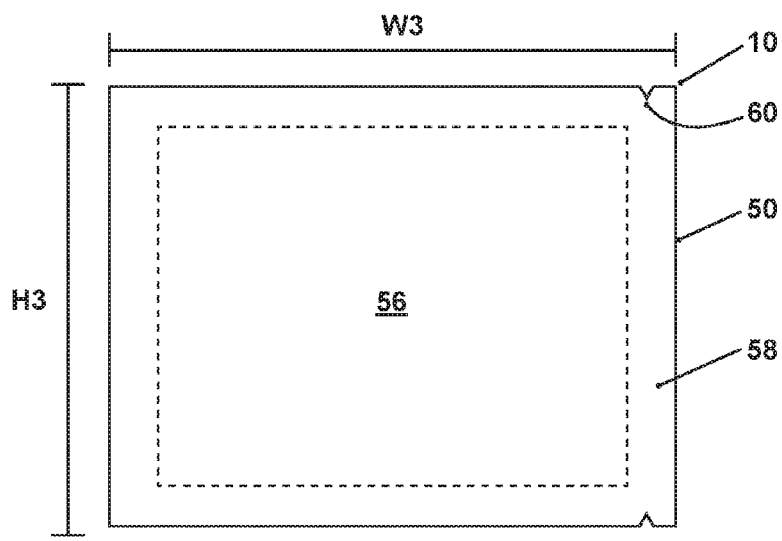
FIG. 1 is a top plan view of an embodiment of a personal hygiene assembly according to the invention, in a sealed configuration.

Certain terminology is used in the foregoing description for convenience and is not intended to be limiting. Words such as "front," "back," "top," and "bottom" designate directions in the drawings to which reference is made. This terminology includes the words specifically noted above, derivatives thereof, and words of similar import. Additionally, the words "a" and "one" are defined as including one or more of the referenced item unless specifically noted. The phrase "at least one of" followed by a list of two or more items, such as "A, B or C," means any individual one of A, B or C, as well as any combination thereof.

A personal hygiene towelette and assembly according to the invention is shown in FIGS. 1-4. As shown, the assembly 10 comprises a towelette 20 and a housing 50.

The towelette 20 is shown in detail in FIGS. 3 and 4, and comprises a textile fabric body 22 impregnated with a consumable cleaning solution. The body 22 is sized to fit within the housing 50, as described in detail below. In the embodiment shown, the body 22 is foldable, and sized to fit within the housing 50 when in the folded configuration of FIG. 3. In one embodiment, the body 22 could have a width W2 in the unfolded configuration of 6 inches, and a height H2 in the unfolded configuration of 3 inches.

As shown, the body 22 comprises a plurality of creases, comprising both width-wise creases 24 and height-wise creases 26. The body 22 is folded along the creases 24, 26 when in the folded configuration of FIG. 4. In the folded configuration, the body could have a width W1 of 1½ inches, and a height H1 of 2 inches. While three height-wise creases 26 and a single width-wise crease 24 are provided in the embodiment shown, it should be understood that these amounts could vary, or the body could be provided with only creases extending in a single direction. Likewise, the dimensions of the body 22 could vary, depending on the size or type of the housing, as well as the desired storage method, as described in detail below.

The textile fabric of the body 22 may be a nonwoven fabric, and optionally a nonwoven fabric formed without binders. The nonwoven fabric may optionally be a three-dimensional nonwoven fabric. For example, the textile fabric could be a thermally bonded nonwoven fabric, or a mechanically bonded nonwoven fabric, such as a needle punched, water-jet, air-jet bonded nonwoven fabric. For example, the body could be formed of a water-jet bonded fabric, such as SONTARA® fabric produced by DUPONT®.

The textile fabric of the body 22 preferably has a high absorbency, and in particular a high hold, so as to permit retention of a sufficient amount of cleaning solution. For example, the textile fabric could be configured to hold at least 4 times its weight in liquid, or 6 times its weight in some embodiments.

The textile fabric of the body 22 may contain at least one absorbent fiber, such as a cellulosic fiber or a protein fiber, so as to encourage absorption and hold of the cleaning solution. In some embodiments the absorbent fiber is a cellulosic fiber, such as cotton, rayon or wood pulp.

The textile fabric of the body 22 may further contain at least one wicking fiber, such as a thermoplastic fiber, so as to encourage wicking and in turn distribution of the cleaning solution throughout the body 22. In some embodiments, the thermoplastic fiber is a polyester fiber.

In some embodiments, the textile fabric of the body 22 contains a blend of the absorbent fiber and the wicking fiber, for example, containing between 40% and 60% of each fiber type. In some embodiments the textile fabric contains a blend composed of 46% polyester and 54% wood pulp.

The body 22 is of a thickness so as to permit absorption of a sufficient amount of cleaning solution, but to also permit folding along the creases 24, 26, allowing the towelette 20 to fit within the housing 50. For example, the body 22 may have a thickness of between 0.250 and 0.350 mils. In some embodiments, the body 22 has a thickness of 0.305 mils when tested according to ASTM Standard D1117.

The body 22 is formed of a fabric having a basis weight to permit absorption of a sufficient amount of cleaning solution, without being excessively heavy or bulky. For example, the body could have a basis weight of between 1.25 and 1.75 oz/yd$^2$. In some embodiments, the body 22 may have a basis weight of 1.50 oz/yd$^2$ when tested according to ASTM Standard D3776.

The body 22 is formed of a fabric having a sufficient grab tensile breaking strength so as to avoid tearing or deformation of the material during wiping. For example, the material of the body 22 could have a tensile breaking strength of at least 20 lbs. in the machine direction and at least 10 lbs. in the cross direction. In some embodiments, the body 22 has a tensile breaking strength of 29 lbs. in the machine direction and 15 lbs. in the cross direction when tested according to ASTM Standard 5034.

The towelette 20 is impregnated with a consumable cleaning solution containing at least one flavoring agent and at least one cleaning agent. The consumable cleaning solution is a non-toxic fluid suitable for contact with the skin and mucous membranes and configured to gently clean the area applied to. The solution is also configured to deposit a flavor upon the area applied to, as described in detail below.

The cleaning agent may be a saline solution, containing at least one salt in a liquid, for example an aqueous suspension containing water, to gently clean the area applied to in a non-irritating manner. For example, the at least one salt could be sodium chloride, as well as other non-toxic salts known in the art.

The consumable cleaning solution further comprises at least one flavoring agent. Flavoring agents known in the art, such as natural flavors, may be employed and utilized to mimic a variety of flavors. In one embodiment, the consumable cleaning solution is provided in a fruit flavor, such as strawberry. The consumable cleaning solution may be provided in other flavors known in the art as well.

The consumable cleaning solution may further comprise at least one sweetening agent. Any type of sweetening agent known in the art could be employed, such as a sugar, sugar alcohol or non-caloric artificial sweetener. For example, the at least one sweetening agent could comprise at least one of glycerin or sucralose, as well as other sweetening agents known in the art.

The consumable cleaning solution may further comprise at least one thickening agent to facilitate deposit of a layer of the consumable cleaning solution, and in turn the flavoring and sweetening agents contained therein, on the area applied to. The thickening agent could be, for example, a hydrophobic agent configured to form a film when applied to the skin of a user. Any type of non-toxic thickening agent known in the art could be employed, such as hydroxyethylcellulose. Other thickening or film-forming agents could be employed as well.

The consumable cleaning solution may further comprise at least one humectant, which may, for example, serve to retain moisture within the consumable cleaning solution and optionally act as a lubricant. In some embodiments, the consumable cleaning solution may comprise glycerin as a humectant, which may also act as a sweetener, as noted above. Other non-toxic humectants known in the art may be employed as well.

The consumable cleaning solution may further comprise at least one preservative. In some embodiments, sodium benzoate, potassium sorbate, gluconolactone or any combination thereof may be employed as a preservative.

In some embodiments, the consumable cleaning solution is configured to be colorless and therefore undetectable absent direct contact with therewith. The consumable cleaning solution is configured to be non-irritating to the skin of most individuals and is therefore of a pH which will not cause such irritation. In one embodiment, the consumable cleaning solution has a pH between 4.5 and 5.5. The consumable cleaning solution my include a non-toxic acid or base to achieve a suitable pH. For example, the consumable cleaning solution may comprise citric acid.

In one embodiment, the consumable cleaning solution comprises a combination of water, glycerin, polysorbate 60, natural flavor, sucralose, hydroxyethylcellulose, potassium sorbate, sodium chloride, citric acid, sodium benzoate, gluconolactone.

The consumable cleaning solution may comprise a variety of other additives, such as fragrances and coloring agents.

Figure 2:
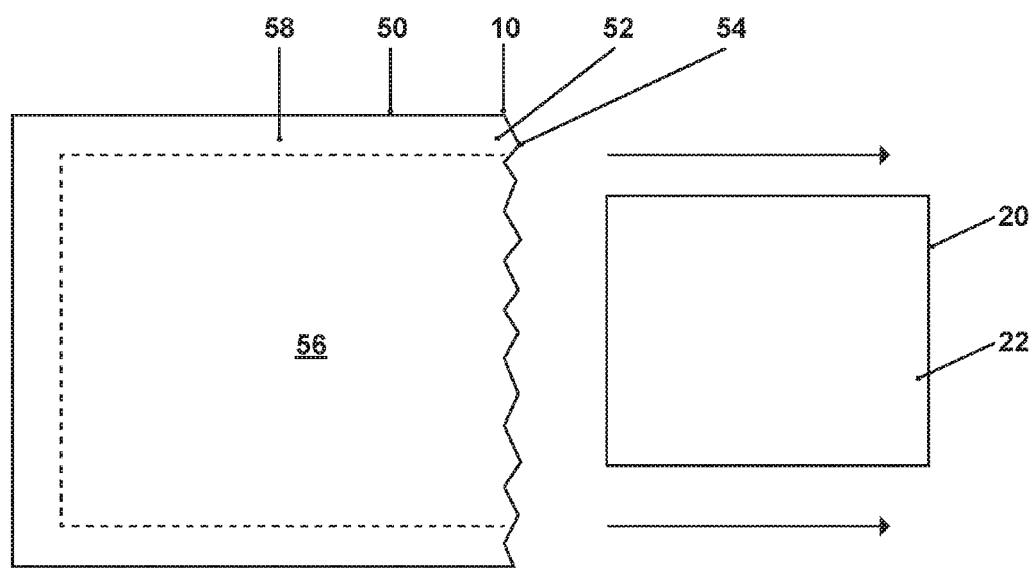
FIG. 2 is a top plan view of the assembly of FIG. 1, with the housing in an unsealed configuration and the towelette removed therefrom.

Referring to FIGS. 1 and 2, an embodiment of a housing 50 according to the invention is shown in detail. In the embodiment shown, the housing 50 is formed as a foil pouch having a first foil layer 52 overlapping a second foil layer 54 and a housing space 56 formed therebetween. The housing space 56 of this embodiment is dimensioned to hold the towelette 20 when in the folded configuration. A sealed region 58 is formed about the edge of the housing 50, surrounding the housing space 56. A seal is formed between the first foil layer 52 and the second foil layer 54, which may be a moisture-tight seal. In some embodiments, each foil layer 52, 54 may include a layer of thermoplastic material facing inward, and a moisture-tight seal formed by heat crimping the housing 50 about the sealed region 58.

The seal of the housing 50 is configured to be irreversibly breakable, such that the towelette 20 housed therein is suitable for a single use, after which a user may dispose of both the towelette 20 and housing 50. In the embodiment shown, the housing 50 comprises a tare notch 60 formed in an outer edge thereof. The tare notch may be formed at any location about the edge of the housing, but in the embodiment shown, the tare notch 60 is in alignment with an area slightly inward from an upper or outer edge of the housing space 56, so that a tare initiated at the tare notch 60 will intersect the housing space 56 without resulting in taring of the towelette 20 housed within.

The housing 50 is dimensioned to be easily and discreetly carried on the person of a user, for example within a user's pocket, purse or wallet. As shown, due to the layered construction, the housing 50 has minimal thickness. In some embodiments, the housing 50 may have a width W3 of 3⅜ inches and a height H3 of 2½ inches. In some embodiments, the housing 50 may be dimensioned to allow multiple assemblies 10 to be stored in a vending or dispensing machine, such as a conventional dispensing machines typically used in public restrooms.

Figure 5:
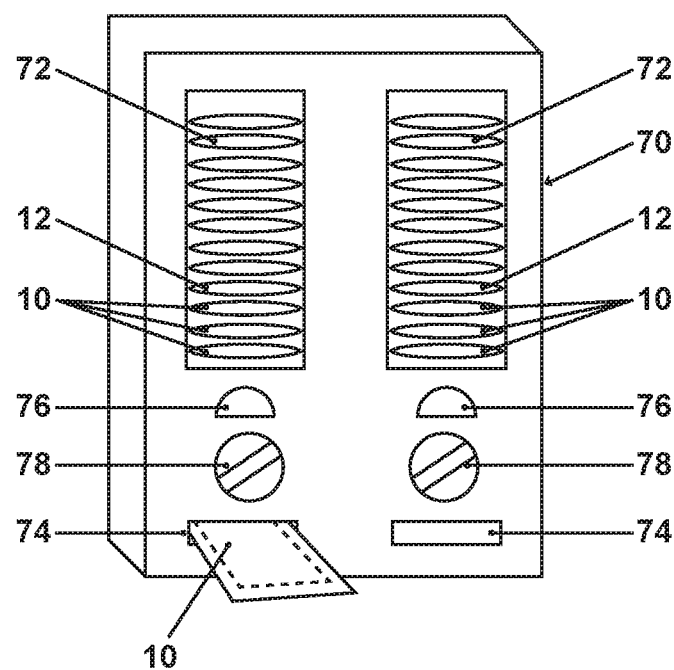
FIG. 5 is a perspective view of a dispensing machine housing a plurality of personal hygiene assemblies according to the invention.

FIG. 5 shows an example of a dispensing machine 70 that may be used with the assemblies 10 of the invention. As shown, the dispensing machine 70 houses a plurality of assemblies 10 in a stacked configuration within an interior thereof. Each stack 12 of assemblies 10 is housed within a channel 72 in communication with a dispensing slot 74 formed at the bottom thereof. The machine 70 comprises a known coin feed 76 and dial 78 dispensing system, wherein by placing a coin within the coin feed 76 a user is permitted to turn the dial 78, resulting a single assembly 10 being dispensed via the dispensing slot 74. Such is the configuration of many conventional dispensing machines known in the art, and the assemblies 10 of the invention can be housed in and dispensed from such machines in place of, or along with, condoms, tissues or feminine hygiene products. While FIG. 5 shows one example of a known type of dispensing machine, it should be understood that the personal hygiene assemblies 10 of the invention could be housed within and dispensed from other types of known dispensing machines as well, and a person of ordinary skill in the art would be capable of selecting a suitable dispensing machine based on the dimensions of the housing 50.

Figure 6:
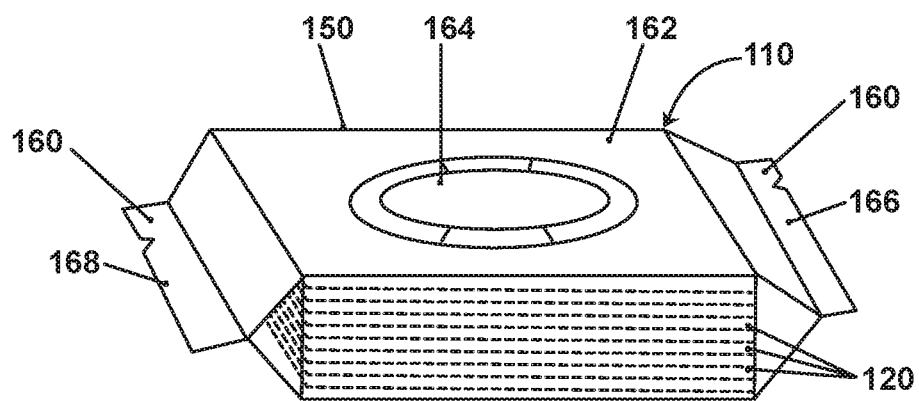
FIG. 6 is a perspective view of another embodiment of a personal hygiene assembly according to the invention, in a sealed configuration.

FIGS. 6-8 illustrate another embodiment of a personal hygiene assembly 110 according to the invention. The embodiment of FIGS. 6-8 is similar to that of FIGS. 1-4 and only the differences will be described in detail. Analogous elements will be designated using the same reference numbers, increased by 100.

As shown in FIG. 6, the housing 150 of this embodiment is configured to house a plurality of towelettes 120 in a stacked configuration. The towelettes 120 of this embodiment may be sized and folded similarly to those of FIGS. 1-4. Alternatively, the towelettes 120 of this embodiment may be sized and folded differently, for example being larger and having fewer creases, due to the lack of size constraints with respect to the housing 150. In the embodiment shown, the towelette 120 is larger than that of FIGS. 1-4 and includes a single width-wise crease 124, as shown in FIG. 8. Alternatively, the towelettes 120 could be provided free of creases and arranged flat in a stacked configuration within the housing 150. Optionally, the towelettes could be joined at the edges thereof, for example, along a perforation, allowing for easy detachment of a single towelette 120.

Referring again to FIG. 6, the housing 150 is formed as a conventional "soft-pack," formed, for example of a thermoplastic material. As shown, the housing 150 comprises a single tubular body 162 that wraps the stack of towelettes 120 housed within. Opposite ends of the body 162 join to form seals 166, 168 at opposite ends of the housing 150. Each of the seals 166, 168 may be formed, for example, by heat crimping. A tare notch 160 is formed in at least one edge, for example within a seal 166 near a side of the housing 150, so as to permit easy taring of the housing 150 to remove the towelettes 120 housed within, while avoiding taring of the towelettes 120 along with the housing. Optionally, a resealable opening 164, for example a conventional flip-top closure, may be formed in an upper surface of the housing 150 to permit removal of one or more towelettes 120 and reclosure of the housing to seal the remaining towelettes 120 therein.

While FIG. 6 shows one example of a soft-pack style housing according to the invention, it should be understood that other soft-pack housings known in the art could be employed as well. The housing 150 of FIG. 6 could be stored, for example, by a user's bedside or within a user's personal bathroom, making a plurality of towelettes 120 easily accessible within the user's home when needed.

While the preferred embodiments of the invention have been described in detail above, the invention is not limited to the specific embodiments described, which should be considered as merely exemplary.

What is claimed is:

1. A personal hygiene towelette comprising:
    a consumable cleaning solution comprising a combination of water, glycerin, polysorbate 60, natural flavor, sucralose, hydroxyethylcellulose, potassium sorbate, sodium chloride, citric acid, sodium benzoate, gluconolactone; and
    a textile fabric body impregnated with the consumable cleaning solution.

2. The personal hygiene towelette of claim 1, wherein the textile fabric body is formed of a nonwoven fabric.

3. The personal hygiene towelette of claim 2, wherein the nonwoven fabric is a three-dimensional nonwoven fabric.

4. The personal hygiene towelette of claim 2, wherein the nonwoven fabric is a mechanically bonded nonwoven fabric.

5. The personal hygiene towelette of claim 4, wherein the nonwoven fabric is a water jet spun fabric.

6. The personal hygiene towelette of claim 1, wherein the textile fabric comprises at least one cellulosic fiber.

7. A personal hygiene assembly comprising:
    A personal hygiene towelette comprising (i) a consumable cleaning solution including a combination of water, glycerin, polysorbate 60, natural flavor, sucralose, hydroxyethylcellulose, potassium sorbate, sodium chloride, citric acid, sodium benzoate, gluconolactone, and (ii) a textile fabric body impregnated with the consumable cleaning solution; and a sealed housing that houses the personal hygiene towelette.

8. The assembly of claim 7, wherein the sealed housing is a foil packet.

9. The assembly of claim 7, wherein the sealed housing comprises a non-resealable, breakable seal.

10. The assembly of claim 7, wherein the foil packet comprises one tare notch.

11. The assembly of claim 7, wherein the sealed housing comprises a moisture-tight seal.

12. A method of genital cleaning comprising:
    providing a personal hygiene assembly comprising:
    a personal hygiene towelette comprising (i) a consumable cleaning solution including a combination of water, glycerin, polysorbate 60, natural flavor, sucralose, hydroxyethylcellulose, potassium sorbate, sodium chloride, citric acid, sodium benzoate, gluconolactone, and (ii) a textile fabric body impregnated with the consumable cleaning solution, and
    a housing that comprises a seal and houses the personal hygiene towelette; breaking the seal and removing the personal hygiene towelette from the housing; and wiping a user's genital area with the personal hygiene towelette, wherein the consumable cleaning solution is deposited on the genital area during wiping.

13. The method of claim 12, further comprising disposing of the personal hygiene assembly after wiping the user's genital area.

\* \* \* \* \*